(12) United States Patent
Qiu

(10) Patent No.: US 12,022,809 B2
(45) Date of Patent: Jul. 2, 2024

(54) AUTOMATIC PET FEEDER

(71) Applicant: JIANGSU ZHONGHENG PET ARTICLES JOINT-STOCK CO., LTD., Yancheng (CN)

(72) Inventor: Bin Qiu, Yancheng (CN)

(73) Assignee: JIANGSU ZHONGHENG PET ARTICLES JOINT-STOCK CO., LTD., Yancheng (CN)

( * ) Notice: Subject to any disclaimer, the term of this patent is extended or adjusted under 35 U.S.C. 154(b) by 113 days.

(21) Appl. No.: 17/851,062

(22) Filed: Jun. 28, 2022

(65) Prior Publication Data

US 2023/0053183 A1 Feb. 16, 2023

(30) Foreign Application Priority Data

Aug. 11, 2021 (CN) .......................... 202110921167.1

(51) Int. Cl.
*A01K 5/02* (2006.01)
*A61L 2/10* (2006.01)

(52) U.S. Cl.
CPC .............. *A01K 5/0275* (2013.01); *A61L 2/10* (2013.01); *A61L 2202/11* (2013.01); *A61L 2202/14* (2013.01)

(58) Field of Classification Search
CPC .................................................. A01K 5/0275
USPC ...................................................... 119/51.11
See application file for complete search history.

(56) References Cited

U.S. PATENT DOCUMENTS

| | | | | |
|---|---|---|---|---|
| 11,712,022 B2 * | 8/2023 | Zhu | ...................... | A01K 5/0291 |
| | | | | 119/51.11 |
| 2016/0000036 A1 * | 1/2016 | Cornwell, Jr. | ....... | A01K 5/0291 |
| | | | | 119/51.11 |
| 2020/0367469 A1 * | 11/2020 | Zhu | ...................... | A01K 5/0291 |
| 2021/0204511 A1 * | 7/2021 | Chen | .................... | A01K 5/0225 |

FOREIGN PATENT DOCUMENTS

| | | | | |
|---|---|---|---|---|
| CN | 207269566 U | | 4/2018 | |
| EP | 0930006 A1 * | | 7/1999 | |
| WO | WO-0124619 A1 * | | 4/2001 | ........... A01K 5/0291 |

* cited by examiner

*Primary Examiner* — Monica L Perry
*Assistant Examiner* — Brittany A Lowery
(74) *Attorney, Agent, or Firm* — Bayramoglu Law Offices LLC

(57) ABSTRACT

An automatic pet feeder includes a food container, a feeder body, and a bottom shell in sequence from top to bottom. A food-container bottom shell in communication with the food container is arranged at a bottom of the food container, and a bottom of the food-container bottom shell is a food supply passage having a gradually narrowing opening. A food releasing assembly is arranged on a side of the food supply passage, and a sliding passage for reciprocating movement of the food releasing assembly is arranged on a sidewall of the food-container bottom shell. A feeder main shell is arranged below the food supply passage, and a food exit assembly is arranged inside the feeder main shell. The food exit assembly includes a food pushing member matching with a food outlet and configured to move in a reciprocating manner below the food supply passage.

20 Claims, 5 Drawing Sheets

AUTOMATIC PET FEEDER

CROSS REFERENCE TO THE RELATED APPLICATIONS

This application is based upon and claims priority to Chinese Patent Application No. 202110921167.1, filed on Aug. 11, 2021, the entire contents of which are incorporated herein by reference.

TECHNICAL FIELD

The present disclosure relates to a feeder, and specifically to an automatic pet feeder, which belongs to the technical field of pet supplies.

BACKGROUND

As people's quality of life improves, more and more people are raising pets at home, which has led to the development of the industry of pet supplies. Among others, pet feeders are a commonly seen type of pet supplies used for daily feeding of pets.

In people's daily lives, everyone is very busy. A pet breeder has to ask another person to take care of his/her pet while he/she is away for a business trip or some other urgent matter, which is very inconvenient. Some breeders may find it troublesome to feed their pets on a regular basis every day. To solve such problems, pet feeders have been developed.

The breeder only needs to put pet food in the feeder, and the rest will be done by the feeder, which serves a certain amount of pet food to the pet on a regular basis every day. Because a large amount of food is put in the feeder at a time, they there is a need of an easy-to-use pet feeder which has good sealing performance and cannot be opened by pets at will, in order to prevent the food from getting wet and ensure that the pets at home do not eat all the food too early.

For example, CN207269566U discloses an automatic feeder mechanism for pets, including a food supply base. A food supply passage is arranged on the food supply base. A blade roller assembly is arranged inside the food supply passage. A food container is arranged at an upper part of the food supply base. A stirring rod is further arranged at a food entrance of the food supply passage. The stirring rod can undergo fan-shaped movement with one end thereof as a fulcrum. In this patent, with the arrangement of the stirring rod, when grains of the pet food support each other and get stuck, the vertical movement of the stirring rod will break such a state of support, to ensure that the food can be supplied normally. However, this feeder mechanism has some drawbacks. For example, the rotation of the stirring rod requires high power, the food exit cannot be opened automatically, and so on.

SUMMARY

An objective of the present disclosure is to provide an automatic pet feeder to solve the above problems of the prior art.

The objective of the present disclosure is achieved by the following technical solution.

An automatic pet feeder, including a food container, a feeder body, and a bottom shell in sequence from top to bottom, and further including a mounting base for mounting, fixing, and receiving parts and components at given positions, a control circuit configured to control operation of electrical components, and a power supply.

A food-container bottom shell in communication with the food container is arranged at a bottom of the food container, and a bottom of the food-container bottom shell is a food supply passage having a gradually narrowing opening. A food releasing assembly is arranged on a side of the food supply passage, and a sliding passage for reciprocating movement of the food releasing assembly is arranged on a sidewall of the food-container bottom shell.

A feeder main shell is arranged below the food supply passage, and a food exit assembly is arranged inside the feeder main shell. The food exit assembly includes a food pushing member matching with a food outlet and configured to move in a reciprocating manner below the food supply passage. The reciprocating movement of the food pushing member is controlled by a transmission mechanism arranged below the food pushing member.

The food pushing member is linked with the food releasing assembly by a food-releasing rotary member, and a moving direction of the food pushing member is opposite to a moving direction of the food releasing assembly.

The transmission mechanism is electrically connected to the control circuit.

The food exit assembly further includes a food exit bottom shell configured to receive the food pushing member and restrict back and forth movement of the food pushing member, the food pushing member is drive-connected with an output end of a driving motor of the transmission mechanism by a food-pushing rotary assembly. Reciprocating movement of the food pushing member inside the food exit bottom shell is realized by the food-pushing rotary assembly.

The food pushing member includes a bottomless frame configured to accommodate pet food, and a space for accommodating the pet food is defined by four side frames of the bottomless frame and the food exit bottom shell. When the food pushing member moves toward the food outlet, the bottomless frame pushes the pet food to move relative to the food exit bottom shell; and when the bottomless frame moves beyond the food exit bottom shell, the pet food falls from the food outlet.

A driving-motor mounting hole is provided at a bottom of the food exit bottom shell.

The food-pushing rotary assembly includes a food-pushing rotary member drive-connected with a bottom of the food pushing member and a food-pushing fixing member configured to drive the food-pushing rotary member, and the food-pushing fixing member is drive-connected with an output shaft of the driving motor.

The transmission mechanism includes a driving motor, and the driving motor is vertically mounted in a driving-motor mounting hole; a horizontal swing arm is fixed on an output shaft of the driving motor, a raised slider is arranged on an upper side of the swing arm, and the slider matches with a sliding groove and is configured to reciprocate in the sliding groove; and a limit protrusion is arranged on the output shaft of the driving motor, the limit protrusion enters into contact with and presses against a limit switch when a movable part is closed, and for each turn of the output shaft, the limit protrusion enters into contact with the limit switch once to transmit a signal to the control circuit to turn off the driving motor; or as another mode of operation of the technical solution of the present disclosure, an annular limit protrusion is arranged on the output shaft of the driving motor, the annular limit protrusion is provided with a notch corresponding to the limit switch, and for each turn of the output shaft, the annular limit protrusion causes the limit switch to be released once to transmit the signal to the control circuit to turn off the driving motor.

The limit switch may be an optical coupling switch, and when the optical coupling switch detects that the limit protrusion blocks light twice, it is determined that one reciprocation is completed.

A brushing soft rubber that is flush with an upper opening of the food pushing member is arranged above the food pushing member, and the brushing soft rubber is configured to retain pet food overflowing the food pushing member in the food-container bottom shell. Further, the brushing soft rubber is arranged in front of the food pushing member along a traveling direction of the food pushing member when being opened.

To provide a better brushing effect, the brushing soft rubber is tilted rearward along the traveling direction of the food pushing member when being opened.

The food releasing assembly is arranged at an opening of the food supply passage, to prevent pet food in the food supply passage from getting stuck. The food releasing assembly includes a food-releasing piece embedded on a sidewall of the food supply passage and movable for a short distance on the sidewall of the food supply passage, and a food-releasing connector for mounting the food-releasing piece; the food-releasing rotary member is arranged on an outer side of the food releasing assembly, the food-releasing rotary member includes a rotating shaft, and a torsion spring configured to restrict a restoring rotation direction of the food-releasing rotary member is sleeved over the rotating shaft; and an upper end of the food-releasing rotary member is movably connected or in contact with the food releasing assembly through a sidewall of the food container, and a lower end of the food-releasing rotary member is movably connected or in contact with the food pushing member.

When the food pushing member is in a closed state, the lower end of the food-releasing rotary member is compressed by the food pushing member to rotate, to drive the food releasing assembly to move toward the food supply passage, the torsion spring is in a compressed state, and the food supply passage is narrowed. When the food pushing member is opened, a lower force arm of the food-releasing rotary member is released, the torsion spring is restored to drive the food releasing assembly to retract, and the food supply passage is widened, to prevent pet food from getting stuck.

The food outlet is arranged on a wall of the feeder body in an opening direction of the food pushing member, a food exit hatch matching with the food outlet is arranged at the food outlet, and the food exit hatch is hingedly connected to the mounting base by an outwardly bent connecting arm and is configured to be opened upward by contacting with and pushing through at least one point on the food pushing member.

The mounting base is further covered by an exterior shell of an arbitrary shape, and a reserved hole is arranged in front of the exterior shell; and the exterior shell matches with a control panel and the food exit hatch to constitute a complete exterior surface.

The exterior shell is mounted as a combination of at least two exterior shell units.

When the food pushing member is opened, a feeding tray is arranged below the food outlet, and pet food from the food outlet falls into the feeding tray for a pet to eat.

An annular decorative piece is arranged between the food container and the feeder body, and the food-container bottom shell is arranged on an inner side of the decorative piece.

At least one pair of food amount detection windows is arranged at a lower portion of the food container, the food amount detection windows are each a transparent piece, the food amount detection windows are respectively arranged on two opposing sides of the food container, an infrared transmitting device and an infrared receiving device are respectively arranged on the sides on which the food amount detection windows are arranged, and when a height of pet food in the food container is lower than the food amount detection windows, the infrared receiving device receives an infrared signal and sends an alarm.

A sterilization mechanism is further arranged on the food container, and the sterilization mechanism is one selected from an ultraviolet sterilization mechanism and a nitrogen-filled sterilization mechanism.

Further, the ultraviolet sterilization mechanism includes an ultraviolet sterilization lamp; at least one ultraviolet sterilization window is arranged at a lower portion of the food container, and the ultraviolet sterilization window is made of quartz glass; the ultraviolet sterilization lamp is arranged on an outer side of the ultraviolet sterilization window; and ultraviolet rays emitted from the ultraviolet sterilization lamp pass through the ultraviolet sterilization window and sterilize pet food in the food container.

The pet feeder further includes a remote control module and/or a power switch, where the remote control module and/or the power switch are/is electrically connected to a controller. The remote control module is one or more selected from a Bluetooth remote control module, an infrared remote control module, and a Wi-Fi remote control module. When powered, the automatic pet feeder is physically turned on or off or remotely turned on or off.

The power supply is a storage battery, an external power supply, or a combination thereof. A microphone port, a display screen, a charging port, and an atmosphere light are further arranged on the exterior shell.

A plurality of suction cups are arranged at a bottom of the bottom shell, and the feeder is fixed to a floor by the suction cups, to prevent the feeder from falling over.

The pet feeder further includes a lid, where the lid includes an upper lid component, a lower lid component, and a lid rotary member configured to open or close the food container, and a soft lid-sealing rubber is arranged on the lid at a position in contact with the food container.

All the electrical components used in the present disclosure are electrically connected to the control circuit, and on/off of the electrical components is controlled by the control circuit.

The technical solution of the present disclosure has the following beneficial effects.

The food releasing assembly is arranged in the food container. The food releasing assembly cooperates with the movement of the food exit assembly. Through the operation of the driving motor, not only the opening and closing of the food exit assembly are realized, but also food can be prevented from getting stuck.

The present disclosure has a sterilizing function, which can ensure the safety of pet food.

The present disclosure can be powered either by a battery or a power supply, and is easier to move and carry.

DETAILED DESCRIPTION OF THE EMBODIMENTS

Figure 1:
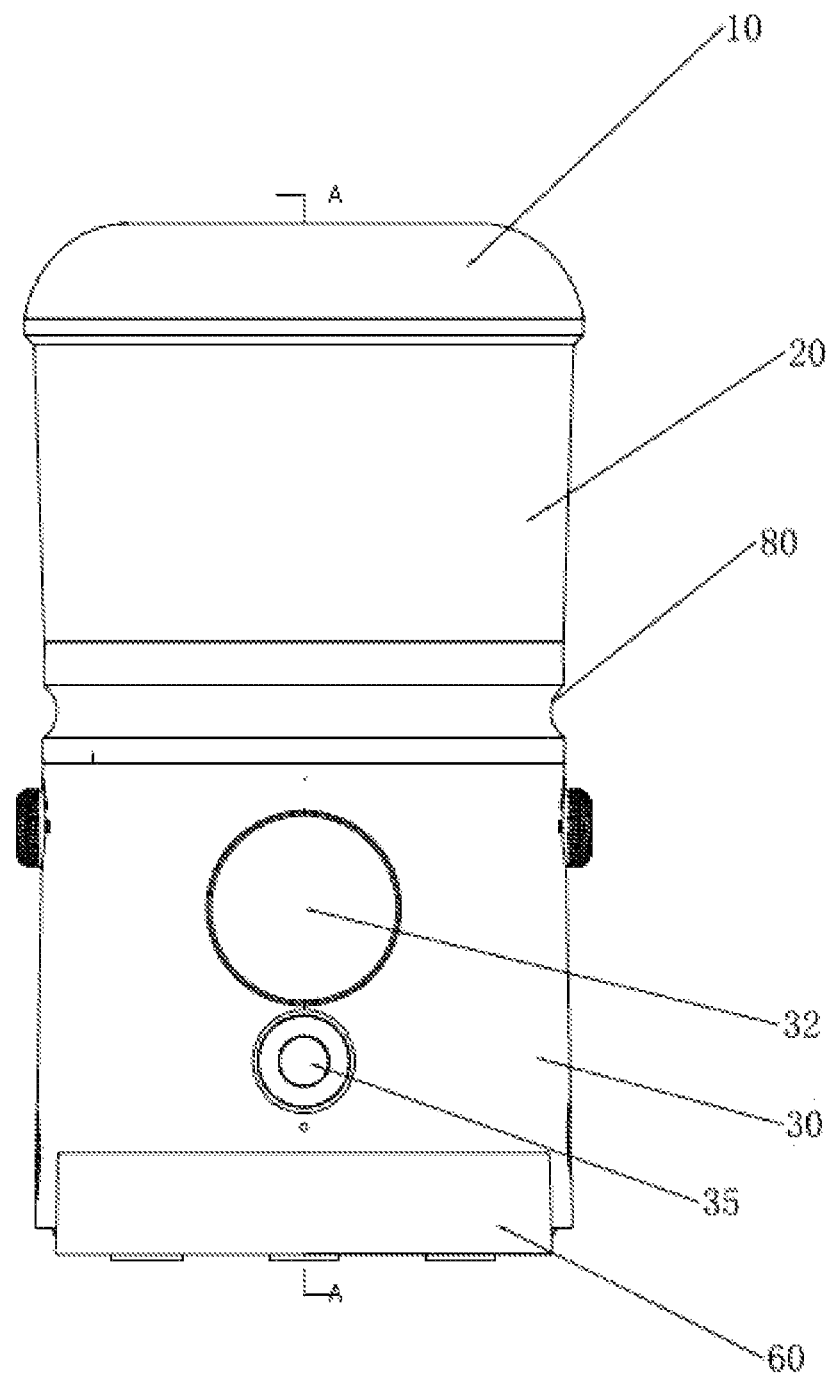
FIG. 1 is a schematic structural diagram of the present disclosure.
Figure 2:
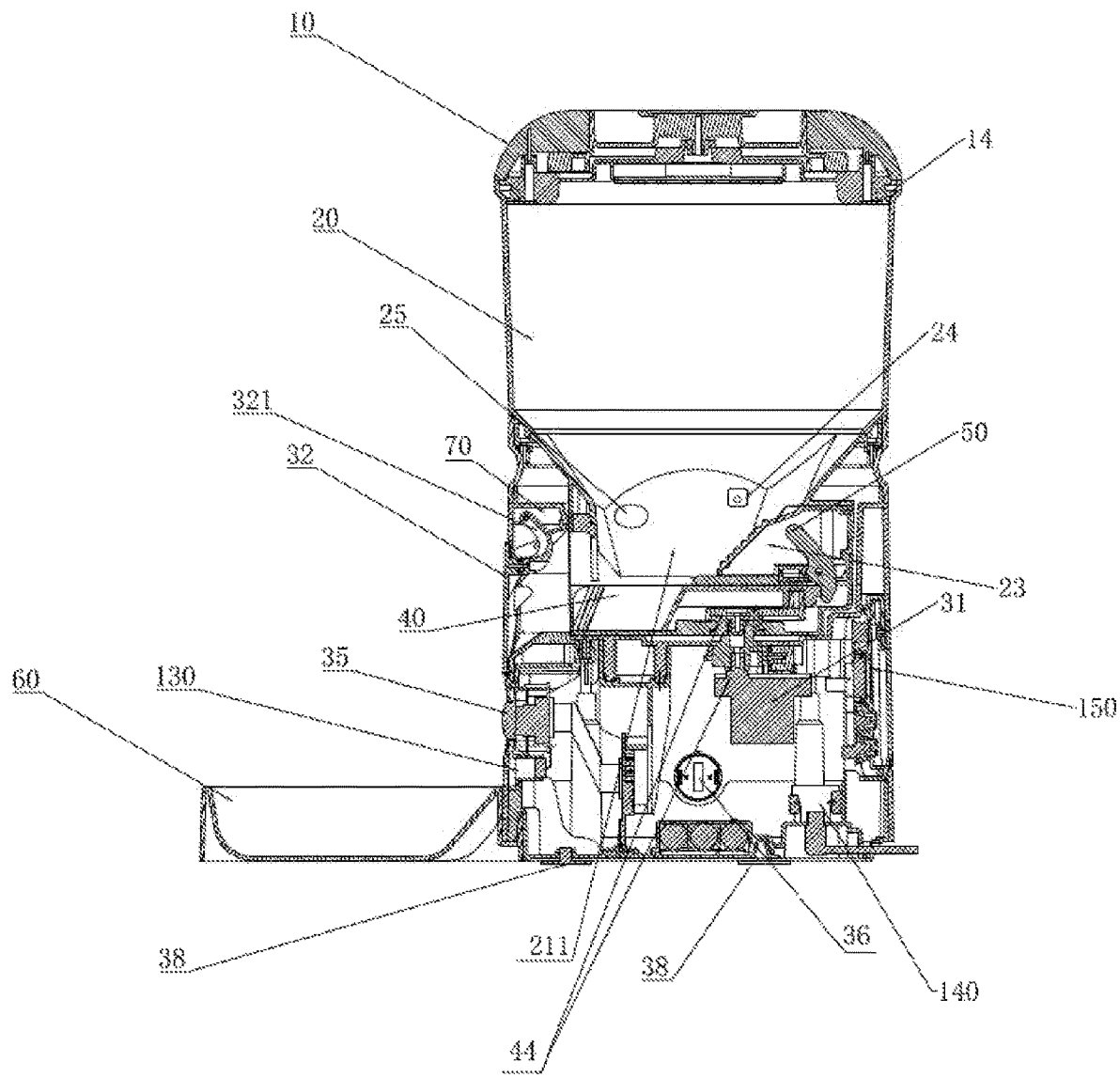
FIG. 2 is a schematic structural cross-sectional view of FIG. 1.
Figure 3:
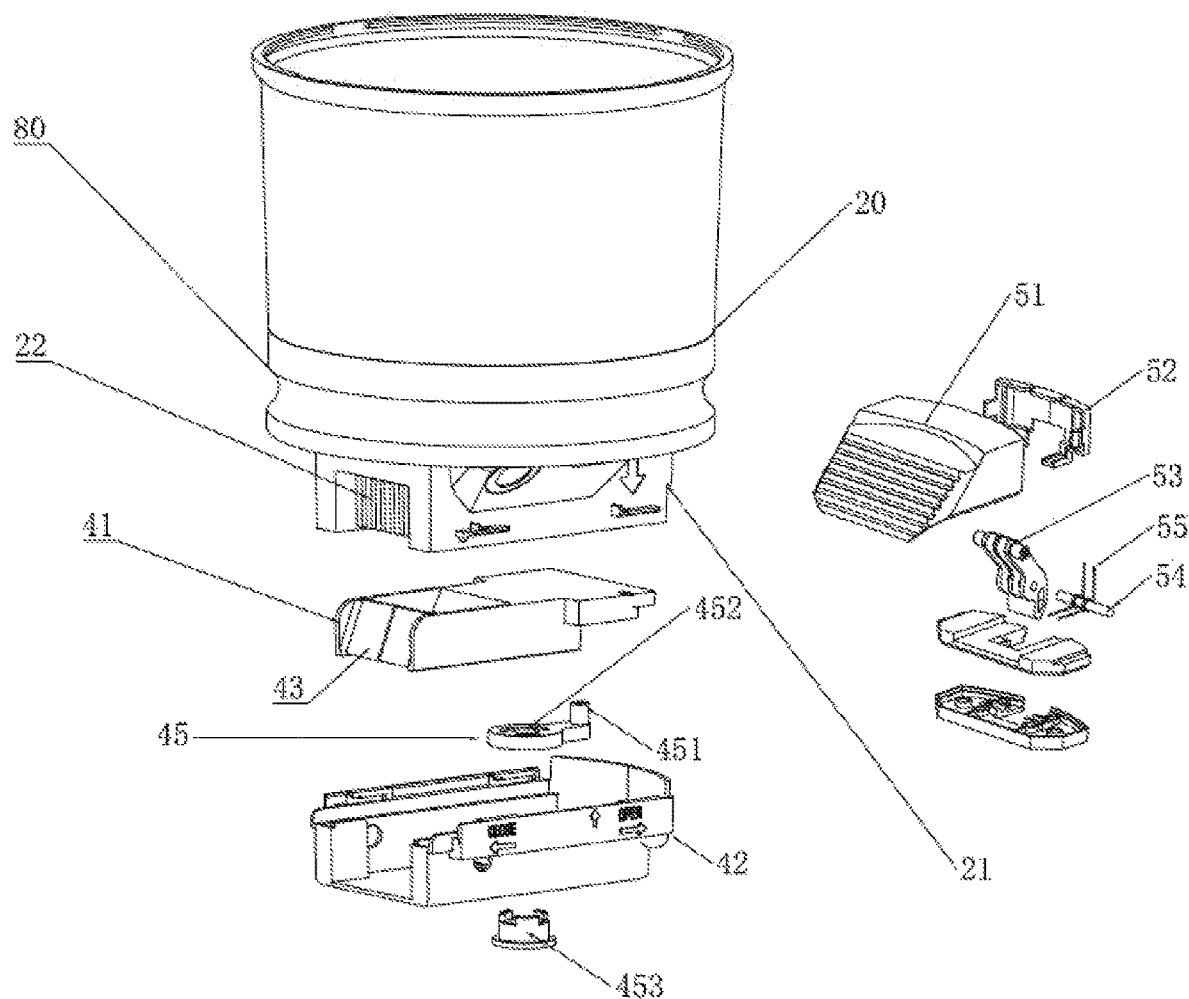
FIG. 3 is a schematic structural diagram of a food container according to the present disclosure.
Figure 4:
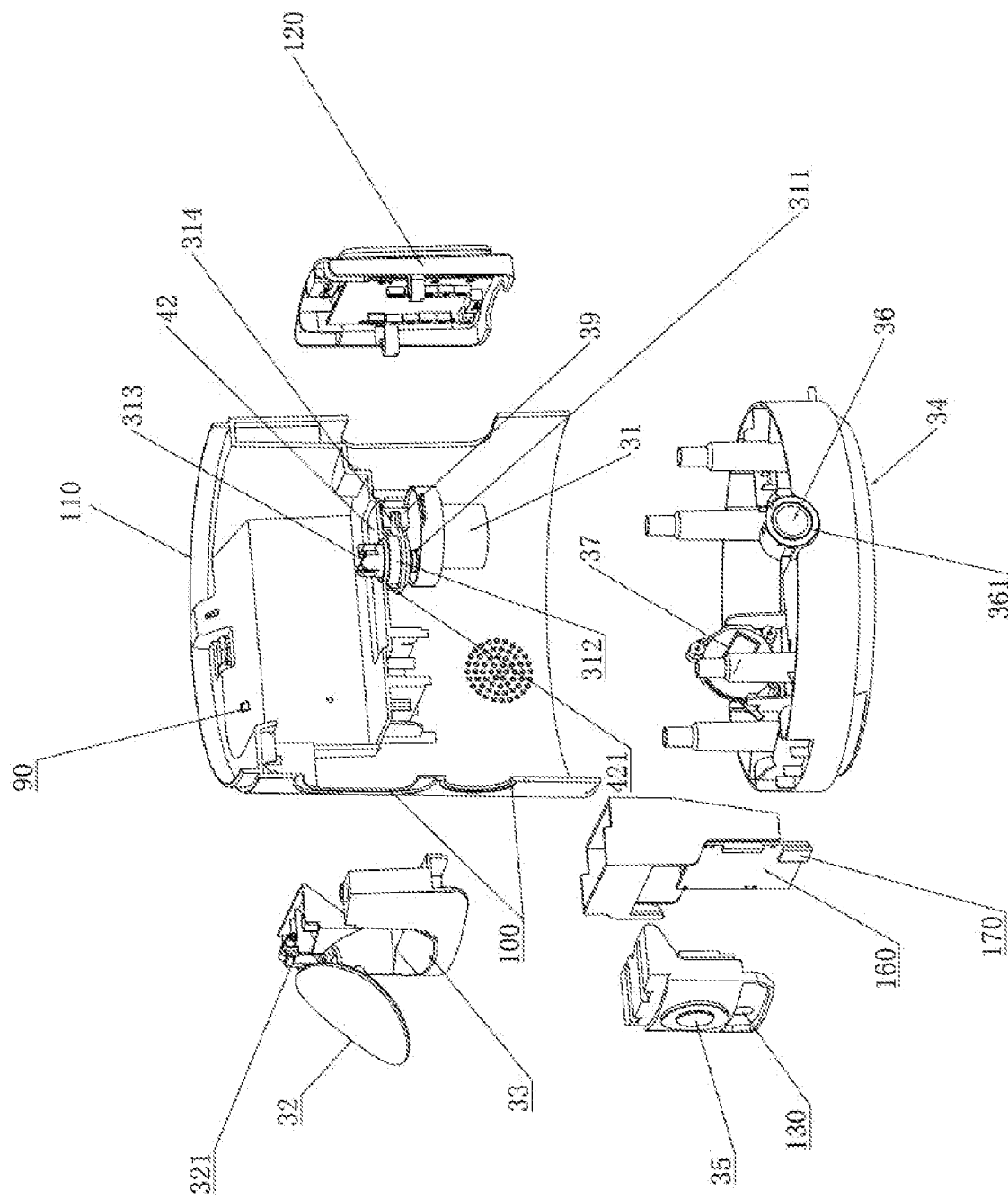
FIG. 4 is a schematic structural diagram of a feeder body according to the present disclosure.
Figure 5:
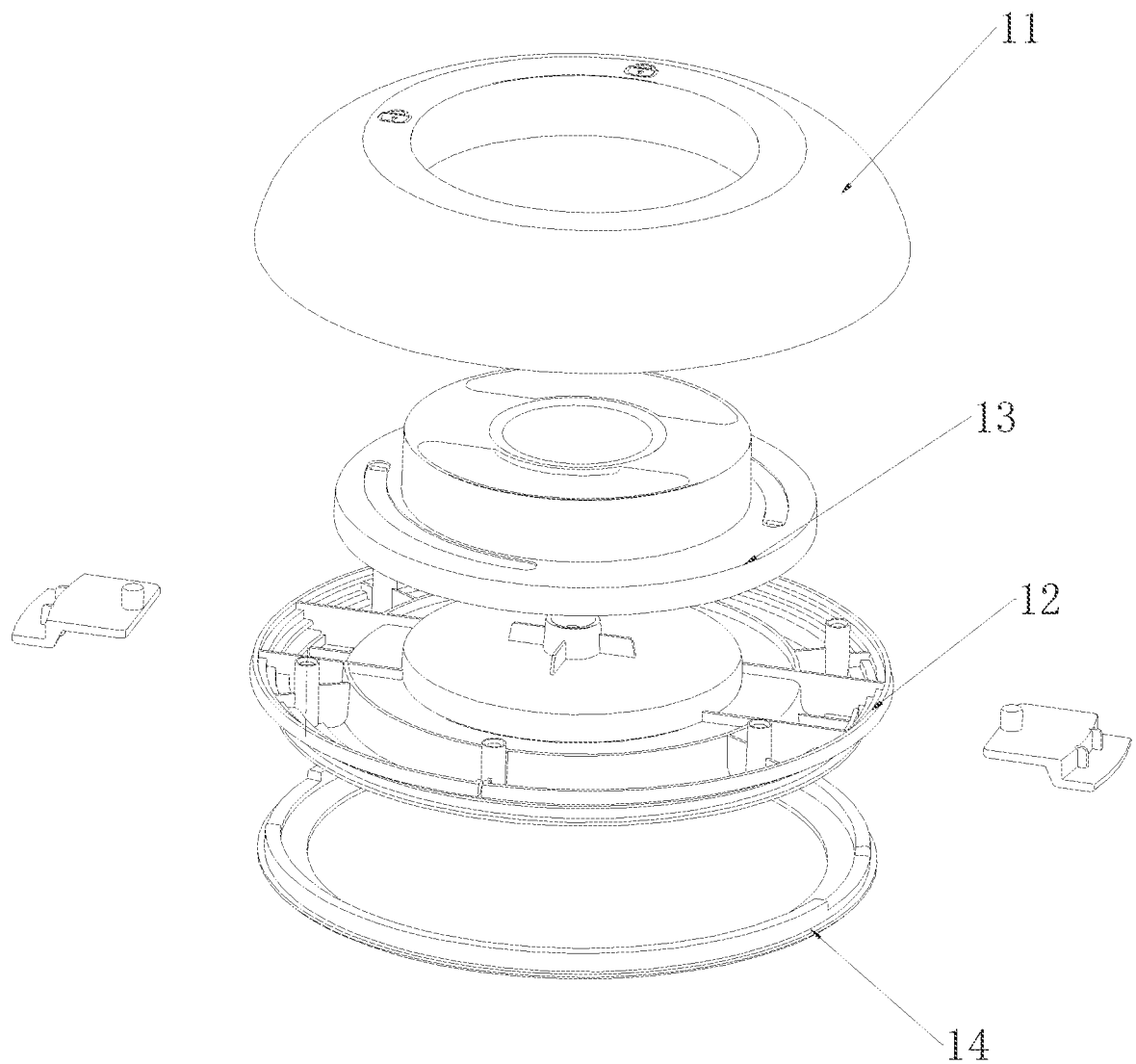
FIG. 5 is a schematic structural diagram of a lid.

The structural features of the present disclosure are further described below in conjunction with the accompanying drawings and specific embodiments. The reference characters in FIGS. 1-5 are defined as follows:

10. lid;
11. upper lid component;
12. lower lid component;
13. lid rotary member;
14. soft lid-sealing rubber;
20. food container;
21. food-container bottom shell;
211. food supply passage having a gradually narrowing opening;
22. brushing soft rubber;
23. sliding passage;
24. food amount detection window;
25. ultraviolet sterilization window;
30. feeder body;
31. driving motor;
311. output shaft;
312. horizontal swing arm;
313. raised slider;
314. limit protrusion;
32. food exit hatch;
321. outwardly bent connecting arm;
33. food outlet;
34. bottom shell;
35. camera;
36. power switch;
361. atmosphere light;
37. speaker;
38. plurality of suction cups;
39. limit switch;
40. food exit assembly;
41. food pushing member;
42. food exit bottom shell;
421. driving-motor mounting hole;
43. bottomless frame;
44. transmission mechanism;
45. food pushing rotary assembly;
451. food pushing rotary member;
452. food pushing fixing member;
453. sliding groove;
50. food releasing assembly;
51. food-releasing piece;
52. food-releasing connector;
53. food-releasing rotary member;
54. rotating shaft;
55. torsion spring;
60. feeding tray;
70. mounting base;
80. annular decorative piece;
90. ultraviolet sterilization lamp;
100. reserved hole arranged in front of the exterior shell;
110. exterior shell unit;
120. control panel;
130. microphone port;
140. charging port;
150. display screen;
160. controller; and
170. remote control module.

As shown in FIG. 1 to FIG. 5, an automatic pet feeder includes a food container 20, a feeder body 30, and a bottom shell 34 in order from top to bottom; and further including a mounting base 70 for mounting, fixing, and receiving parts and components at given positions, a control circuit configured to control operation of electrical components, and a power supply.

A food-container bottom shell 21 in communication with the food container 20 is arranged at a bottom of the food container 20, and a bottom of the food-container bottom shell 21 is a food supply passage having a gradually narrowing opening 211. A food releasing assembly 50 is arranged on a side of the food supply passage, and a sliding passage 23 for reciprocating movement of the food releasing assembly 50 is arranged on a sidewall of the food-container bottom shell 21.

A feeder main shell is arranged below the food supply passage, and a food exit assembly 40 is arranged inside the feeder main shell. The food exit assembly 40 includes a food pushing member matching with a food outlet and configured to move in a reciprocating manner below the food supply passage. The reciprocating movement of the food pushing member is controlled by a transmission mechanism 44 arranged below the food pushing member.

The food pushing member is linked with the food releasing assembly 50 by a food-releasing rotary member 53, and a moving direction of the food pushing member is opposite to a moving direction of the food releasing assembly 50.

The transmission mechanism 44 is electrically connected to the control circuit.

The food exit assembly 40 further includes a food exit bottom shell 42 configured to receive the food pushing member and restrict back and forth movement of the food pushing member, the food pushing member is drive-connected with an output end of a driving motor 31 of the transmission mechanism 44 by a food-pushing rotary assembly. Reciprocating movement of the food pushing member inside the food exit bottom shell 42 is realized by the food-pushing rotary assembly.

The food pushing member includes a bottomless frame 43 configured to accommodate pet food, and a space for accommodating the pet food is defined by four side frames of the bottomless frame 43 and the food exit bottom shell 42. When the food pushing member moves toward the food outlet, the bottomless frame 43 pushes the pet food to move relative to the food exit bottom shell 42; and when the bottomless frame 43 moves beyond the food exit bottom shell 42, the pet food falls from the food outlet.

A driving-motor mounting hole 421 is provided at a bottom of the food exit bottom shell 42.

The food-pushing rotary assembly includes a food-pushing rotary member drive-connected with a bottom of the food pushing member and a food-pushing fixing member configured to drive the food-pushing rotary member, and the food-pushing fixing member is drive-connected with an output shaft 311 of the driving motor 31.

The transmission mechanism 44 includes the driving motor 31, and the driving motor 31 is vertically mounted in a driving-motor mounting hole 421; a horizontal swing arm 312 is fixed on an output shaft 311 of the driving motor 31, a raised slider 313 is arranged on an upper side of the swing arm, and the slider matches with a sliding groove 453 and is configured to reciprocate in the sliding groove 453; and a limit protrusion 314 is arranged on the output shaft 311 of the driving motor 31, the limit protrusion 314 enters into contact with and presses against a limit switch 39 when a movable part is closed, and for each turn of the output shaft 311, the limit protrusion 314 enters into contact with the limit switch 39 once to transmit a signal to the control circuit to turn off the driving motor 31; or as another mode of operation of the technical solution of the present disclosure, an annular limit protrusion 314 is arranged on the output shaft 311 of the driving motor 31, the limit protrusion 314 is provided with a notch corresponding to the limit switch 39, and for each turn of the output shaft 311, the limit protrusion 314 causes the limit switch 39 to be released once to transmit the signal to the control circuit to turn off the driving motor 31.

The limit switch 39 may be an optical coupling switch, and when the optical coupling switch detects that the limit protrusion 314 blocks light twice, it is determined that one reciprocation is completed.

A brushing soft rubber 22 that is flush with an upper opening of the food pushing member is arranged above the food pushing member, and the brushing soft rubber 22 is configured to retain pet food overflowing the food pushing member in the food-container bottom shell 21. Further, the brushing soft rubber 22 is arranged in front of the food pushing member along a traveling direction of the food pushing member when being opened.

To provide a better brushing effect, the sliding passage 23 is tilted rearward along the traveling direction of the food pushing member when being opened.

The food releasing assembly 50 is arranged at an opening of the food supply passage, to prevent pet food in the food supply passage from getting stuck. The food releasing assembly 50 includes a food-releasing piece 51 embedded on a sidewall of the food supply passage and movable for a short distance on the sidewall of the food supply passage, and a food-releasing connector 52 for mounting the food-releasing piece 51; the food-releasing rotary member 53 is arranged on an outer side of the food releasing assembly 50, the food-releasing rotary member 53 includes a rotating shaft 54, and a torsion spring 55 configured to restrict a restoring rotation direction of the food-releasing rotary member 53 is sleeved over the rotating shaft 54; and an upper end of the food-releasing rotary member 53 is movably connected or in contact with the food releasing assembly 50 through a sidewall of the food container 20, and a lower end of the food-releasing rotary member 53 is movably connected or in contact with the food pushing member.

When the food pushing member is in a closed state, the lower end of the food-releasing rotary member 53 is compressed by the food pushing member to rotate, to drive the food releasing assembly 50 to move toward the food supply passage, the torsion spring 55 is in a compressed state, and the food supply passage is narrowed. When the food pushing member is opened, a lower force arm of the food-releasing rotary member 53 is released, the torsion spring 55 is restored to drive the food releasing assembly 50 to retract, and the food supply passage is widened, to prevent pet food from getting stuck.

The food outlet 33 is arranged on a wall of the feeder body 30 in an opening direction of the food pushing member, a food exit hatch 32 matching with the food outlet 33 is arranged at the food outlet 33, and the food exit hatch 32 is hingedly connected to the mounting base 70 by an outwardly bent connecting arm 321 and is configured to be opened upward by contacting with and pushing through at least one point on the food pushing member.

The mounting base 70 is further covered by an exterior shell of an arbitrary shape, and a reserved hole 100 is arranged in front of the exterior shell; and the exterior shell matches with a control panel 120 and the food exit hatch 32 to constitute a complete exterior surface.

The exterior shell is mounted as a combination of at least two exterior shell units 110.

When the food pushing member is opened, a feeding tray 60 is arranged below the food outlet 33, and pet food from the food outlet 33 falls into the feeding tray 60 for a pet to eat.

An annular decorative piece 80 is arranged between the food container 20 and the feeder body 30, and the food-container bottom shell 21 is arranged on an inner side of the decorative piece.

At least one pair of food amount detection windows 24 is arranged at a lower portion of the food container 20, the food amount detection windows 24 are each a transparent piece, the food amount detection windows 24 are respectively arranged on two opposing sides of the food container 20, an infrared transmitting device and an infrared receiving device are respectively arranged on the sides on which the food amount detection windows 24 are arranged, and when a height of pet food in the food container 20 is lower than the food amount detection windows 24, the infrared receiving device receives an infrared signal and sends an alarm.

A sterilization mechanism is further arranged on the food container 20, and the sterilization mechanism is one selected from an ultraviolet sterilization mechanism and a nitrogen-filled sterilization mechanism.

Further, the ultraviolet sterilization mechanism includes an ultraviolet sterilization lamp 90; at least one ultraviolet sterilization window 25 is arranged at a lower portion of the food container 20, and the ultraviolet sterilization window 25 is made of quartz glass; the ultraviolet sterilization lamp 90 is arranged on an outer side of the ultraviolet sterilization window 25; and ultraviolet rays emitted from the ultraviolet sterilization lamp 90 pass through the ultraviolet sterilization window 25 and sterilize pet food in the food container 20.

The pet feeder further includes a remote control module 170 and/or a power switch 36, where the remote control module 170 and/or the power switch 36 are/is electrically connected to a controller 160. The remote control module 170 is one or more selected from a Bluetooth remote control module 170, an infrared remote control module 170, and a Wi-Fi remote control module 170. When powered, the automatic pet feeder is physically turned on or off or remotely turned on or off.

The power supply is a storage battery, an external power supply, or a combination thereof. A microphone port 130, a display screen 150, a charging port 140, and an atmosphere light 361 are further arranged on the exterior shell.

A plurality of suction cups 38 are arranged at a bottom of the bottom shell 34, and the feeder is fixed to a floor by the suction cups 38, to prevent the feeder from falling over.

The pet feeder further includes a lid 10, where the lid 10 includes an upper lid component 11, a lower lid component 12, and a lid rotary member 13 configured to open or close the food container 20, and a soft lid-sealing rubber 14 is arranged on the lid 10 at a position in contact with the food container 20.

It should be noted that the implementations and embodiments of the present disclosure are described in detail, but it can be readily understood by those skilled in the art that a variety of variations can be made in practice without departing from the specific technical features and effects of the present disclosure. Therefore, all such variations are encompassed within the scope of the present disclosure. For example, in the specification or the drawings, the terms described along with different terms which are broader or synonymous may be substituted with different terms at least once in any portion of the specification or the drawings.

What is claimed is:

1. An automatic pet feeder, comprising a food container, a feeder body, and a bottom shell in sequence from top to bottom, and further comprising a mounting base for mounting, fixing, and receiving parts and components at given positions, a control circuit configured to control operation of electrical components, and a power supply, wherein
a food-container bottom shell in communication with the food container is arranged at a bottom of the food container, and a bottom of the food-container bottom shell comprises a food supply passage having a gradually narrowing opening;
a food releasing assembly is arranged on a side of the food supply passage, and a sliding passage for reciprocating movement of the food releasing assembly is arranged on a sidewall of the food-container bottom shell;
a feeder main shell is arranged below the food supply passage, and a food exit assembly is arranged inside the feeder main shell;
the food exit assembly comprises a food pushing member, wherein the food pushing member matches with a food outlet and is configured to move in a reciprocating manner below the food supply passage;
reciprocating movement of the food pushing member is controlled by a transmission mechanism arranged below the food pushing member;
the food pushing member is linked with the food releasing assembly by a food-releasing rotary member, and a moving direction of the food pushing member is opposite to a moving direction of the food releasing assembly; and
the transmission mechanism is electrically connected to the control circuit.

2. The automatic pet feeder according to claim 1, wherein the food exit assembly further comprises a food exit bottom shell configured to receive the food pushing member and restrict back and forth movement of the food pushing member,
the food pushing member is drive-connected with an output shaft of a driving motor of the transmission mechanism by a food-pushing rotary assembly, and
the reciprocating movement of the food pushing member inside the food exit bottom shell is realized by the food-pushing rotary assembly.

3. The automatic pet feeder according to claim 2, wherein the food pushing member comprises a bottomless frame configured to accommodate pet food, and a space for accommodating the pet food is defined by four side frames of the bottomless frame and the food exit bottom shell;
when the food pushing member moves toward the food outlet, the bottomless frame pushes the pet food to move relative to the food exit bottom shell; and
when the bottomless frame moves beyond the food exit bottom shell, the pet food falls from the food outlet.

4. The automatic pet feeder according to claim 2, wherein the food-pushing rotary assembly comprises a food-pushing rotary member drive-connected with a bottom of the food pushing member, and a food-pushing fixing member configured to drive the food-pushing rotary member, and the food-pushing fixing member is drive-connected with the output shaft of the driving motor.

5. The automatic pet feeder according to claim 3, wherein a driving-motor mounting hole is provided at a bottom of the food exit bottom shell;
the transmission mechanism comprises a driving motor, and the driving motor is vertically mounted in the driving-motor mounting hole;
a horizontal swing arm is fixed on an output shaft of the driving motor, a raised slider is arranged on an upper side of the horizontal swing arm, and the raised slider matches with a sliding groove and is configured to reciprocate in the sliding groove; and
a limit protrusion is arranged on the output shaft of the driving motor.

6. The automatic pet feeder according to claim 5, wherein the limit switch is an optical coupling switch, and when the optical coupling switch detects that the limit protrusion blocks light twice, it is determined that one reciprocation is completed.

7. The automatic pet feeder according to claim 1, wherein a brushing soft rubber is flush with an upper opening of the food pushing member and is arranged above the food pushing member;
the brushing soft rubber is configured to retain pet food overflowing the food pushing member in the food-container bottom shell; and
the brushing soft rubber is arranged in front of the food pushing member along a traveling direction of the food pushing member when the food pushing member is opened.

8. The automatic pet feeder according to claim 1, wherein the food releasing assembly comprises a food-releasing piece and a food-releasing connector, wherein the food-releasing piece is embedded on a sidewall of the food supply passage and is movable for a short distance on the sidewall of the food supply passage, and the food-releasing connector is configured for mounting the food-releasing piece;
the food-releasing rotary member is arranged on an outer side of the food releasing assembly, the food-releasing rotary member comprises a rotating shaft;
a torsion spring configured to restrict a restoring rotation direction of the food-releasing rotary member is sleeved over the rotating shaft; and
an upper end of the food-releasing rotary member is movably connected or in contact with the food releasing assembly through a sidewall of the food container, and a lower end of the food-releasing rotary member is movably connected or in contact with the food pushing member.

9. The automatic pet feeder according to claim 1, wherein the food outlet is arranged on a wall of the feeder body in an opening direction of the food pushing member,
a food exit hatch matching with the food outlet is arranged at the food outlet,
the food exit hatch is hingedly connected to the mounting base by an outwardly bent connecting arm, and
the food exit hatch is configured to be opened upward by contacting with and pushing through at least one point on the food pushing member.

10. The automatic pet feeder according to claim 9, wherein
the mounting base is further covered by an exterior shell of an arbitrary shape, and a reserved hole is arranged in front of the exterior shell; and
the exterior shell matches with a control panel and the food exit hatch to constitute a complete exterior surface.

11. The automatic pet feeder according to claim 10, wherein the exterior shell is mounted as a combination of at least two exterior shell units.

12. The automatic pet feeder according to claim 1, wherein when the food pushing member is opened, a feeding tray is arranged below the food outlet, and pet food from the food outlet falls into the feeding tray for a pet to eat.

13. The automatic pet feeder according to claim 1, wherein an annular decorative piece is arranged between the food container and the feeder body, and the food-container bottom shell is arranged on an inner side of the annular decorative piece.

14. The automatic pet feeder according to claim 1, wherein
 at least one pair of food amount detection windows is arranged at a lower portion of the food container,
 the at least one pair of food amount detection windows is each a transparent piece,
 the at least one pair of food amount detection windows is respectively arranged on two opposing sides of the food container.

15. The automatic pet feeder according to claim 1, wherein a sterilization mechanism is further arranged on the food container, and the sterilization mechanism is one selected from an ultraviolet sterilization mechanism and a nitrogen-filled sterilization mechanism.

16. The automatic pet feeder according to claim 15, wherein
 the ultraviolet sterilization mechanism comprises an ultraviolet sterilization lamp;
 at least one ultraviolet sterilization window is arranged at a lower portion of the food container, and the ultraviolet sterilization window is made of quartz glass;
 the ultraviolet sterilization lamp is arranged on an outer side of the at least one ultraviolet sterilization window; and
 ultraviolet rays emitted from the ultraviolet sterilization lamp pass through the at least one ultraviolet sterilization window and sterilize pet food in the food container.

17. The automatic pet feeder according to claim 1, further comprising a remote control module and/or a power switch, wherein
 the remote control module and/or the power switch are/is electrically connected to a controller;
 the remote control module is one or more selected from a Bluetooth remote control module, an infrared remote control module, and a Wi-Fi remote control module; and
 when powered, the automatic pet feeder is physically turned on or off, or remotely turned on or off.

18. The automatic pet feeder according to claim 10, wherein the power supply is a storage battery, an external power supply, or a combination thereof; and a microphone port, a display screen, a charging port, and an atmosphere light are further arranged on the exterior shell.

19. The automatic pet feeder according to claim 1, wherein a plurality of suction cups are arranged at a bottom of the bottom shell, and the automatic pet feeder is fixed to a floor by the plurality of suction cups, to prevent the automatic pet feeder from falling over.

20. The automatic pet feeder according to claim 1, further comprising a lid, wherein
 the lid comprises an upper lid component, a lower lid component, and a lid rotary member configured to open or close the food container, and
 a soft lid-sealing rubber is arranged on the lid at a position in contact with the food container.

\* \* \* \* \*